(12) United States Patent
Weidner et al.

(10) Patent No.: US 6,566,405 B2
(45) Date of Patent: *May 20, 2003

(54) **SYNERGISTIC COMPOSITIONS CONTAINING AROMATIC COMPOUNDS AND TERPENOIDS PRESENT IN *ALPINIA GALANGA***

(75) Inventors: Morten Sloth Weidner, Virum (DK); Morten Just Petersen, Verlose (DK); Nina Worm Jensen, Koge (DK)

(73) Assignee: Eurovita A/S, Karlslunde (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 18 days.

(21) Appl. No.: 09/370,331

(22) Filed: Aug. 6, 1999

(65) Prior Publication Data

US 2002/0086906 A1 Jul. 4, 2002

Related U.S. Application Data

(63) Continuation-in-part of application No. PCT/DK99/00213, filed on Apr. 16, 1999.

(30) Foreign Application Priority Data

Apr. 16, 1998 (DK) .............................................. 0532/98
Oct. 20, 1998 (DK) ......................................... 1998 01344

(51) Int. Cl.⁷ ...................... A61K 31/05; A61K 31/015; A61K 31/36
(52) U.S. Cl. ........................ 514/733; 514/765; 514/456
(58) Field of Search ................................ 514/733, 765, 514/456

(56) References Cited

U.S. PATENT DOCUMENTS 5,587,459 A * 12/1996 Uckun ...................... 530/391.1
5,683,698 A * 11/1997 Chavali et al. ........... 424/195.1
6,203,839 B1 * 3/2001 Bachmann et al.

FOREIGN PATENT DOCUMENTS

| DE | 196 44 422 | 4/1998 | .......... A61K/31/19 |
| JP | 09301988 | * 11/1997 | |
| JP | 1087418 | * 4/1998 | |
| WO | WO 94/28895 | 12/1994 | ......... A61K/31/405 |
| WO | 9739355 | * 10/1997 | |
| WO | WO9805346 | * 2/1998 | |

OTHER PUBLICATIONS

Hammond et al, Antigen enhanced glucosamine . . . , Journal of Immunology, 1975, vol. 115/4, pp. 914–921.*
Janssen et al., Planta Medica, 6:507–511, 1985.
Pooter et al., Phytochemistry, 24:1:93–96, 1985.
Takeuchi, JP 4–23967, 1992 (abstract).
Yu et al., Zhongyao Tongbao, 13:6: 354–356, 1988 (abstract).
Mori et al., Nippon Shokuhin Kagaku Kogaku Kaishi, 42:12:989–995, 1995 (abstract).
Watanabe et al., Biosci., Biotechnol., Biochem. 58:8:1566–1567, 1995 (abstract).
Murakkaimi et al., Cancer Conference 12$^{th}$ Asia Pacific, p. 64, Singapore, 10/17–10/20, 1995 (abstract).
Kumar, Clinical Medicine, Third Edition, Chapter 2, pp. 147–152.

* cited by examiner

Primary Examiner—William R. A. Jarvis
Assistant Examiner—Vickie Kim
(74) Attorney, Agent, or Firm—Darby & Darby

(57) ABSTRACT

Novel compositions of matter containing aromatic compounds and terpenoids which are present in and may preferably be derived from the plant *Alpinia galanga* (Zingiberaceae) show synergistic effects with respect to immunomodulation, and they significantly suppress hypersensitivity reactions. Thus they are used for preparing medicaments for these purposes and, more specifically, for the treatment or prevention of IgE mediated allergic reactions and conditions, such as asthma, allergic rhinitis, a topic eczema or anaphylaxis, and autoimmune disorders, such as Crohn's disease, ulcerative colitis, rheumatoid arthritis or psoriasis, as well as for the alleviation of pain. They can for example be formulated into pharmaceuticals, cosmetics or dietary supplements. A method of preparing such compositions from *Alpinia galanga* is also described.

10 Claims, No Drawings

SYNERGISTIC COMPOSITIONS CONTAINING AROMATIC COMPOUNDS AND TERPENOIDS PRESENT IN *ALPINIA GALANGA*

CROSS-REFERENCE TO RELATED APPLICATIONS

This application is a continuation-in-part of International Application PCT/DK99/00213 filed Apr. 16, 1999, the entire disclosure of which is also incorporated herein by reference.

FIELD OF THE INVENTION

The present invention relates to novel compositions of matter containing aromatic compounds and terpenoids which are present in and may preferably be derived from the plant *Alpinia galanga* (Zingiberaceae), and more specifically to novel pharmaceuticals, cosmetics or dietary supplements containing such compositions. Furthermore the invention relates to the use of the compositions for preparing medicaments for the treatment or prevention of hypersensitivity reactions and diseases associated with hypersensitivity reactions. The invention also relates to a method of preparing such compositions from *Alpinia galanga*.

BACKGROUND OF THE INVENTION

*Alpinia galanga* (L.), family Zingiberaceae, commonly known as Greater Galangal or Java Galangal, is cultivated and grows wild in Asia. The herb is rhizomatic, 1.8–2.1 m in height with oblong glabrous leaves and greenish white flowers. The fruits are orange-red capsules. The plant is also known under the name *Languas galanga*, especially in Thailand, and here it is locally called Katuk karohinee.

In relation to the present invention the term "*Alpinia galanga*" refers to any variety of *Alpinia galanga* or *Languas galanga* found anywhere in the world.

The volatile oil of *Alpinia galanga* can be obtained by steam distillation of the rhizome. It consists primarily of terpenoids with 1,8-cineol as the most abundant compound. Other major terpenoids are: α-pinene, β-pinene, limonene, α-terpineol, terpene-4-ol, and trans-β-farnesene.

Another important class of chemicals in *Alpinia galanga* are aromatic compounds. The quantitatively dominating compound of this class is 1'-acetoxychavicol acetate. Other aromatic constituents are: 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol.

Among the components of *Alpinia galanga* several have been shown to exert pharmacological actions. Thus, Janssen and Scheffer found that 1'-acetoxychavicol acetate is anti fungal (Janssen, A. M. and Scheffer, J. J. C., Planta Medica, pp. 507–511, 1985). Furthermore Watanabe et al found that 1'-acetoxychavicol acetate inhibits phagocytosis of peritoneal macrophages (Watanabe, N. et al, Biosci., Biotechnol., Biochem., vol 59 (8), pp. 1566–67, 1995).

Extracts or concentrates of *Alpinia galanga* containing synergistic compositions of terpenoids and aromatic compounds have not previously been described.

Hypersensitivity is defined as a state of altered reactivity in which the body reacts with an exaggerated immune response to a substance (antigen). Hypersensitivity may be caused by exogenous or endogenous antigens.

Hypersensitivity reactions underlie a large number of diseases. Amongst these allergic and autoimmune conditions are of great importance. A classification of hypersensitivity diseases is given by Parveen Kumar and Michael Clark in the textbook "Clinical Medicine" (3rd edition, 1994, pp. 147–150, Bailliére Tindall, London).

Type I hypersensitivity reactions (IgE mediated allergic reactions) are caused by allergens (specific exogenous antigens), e.g. pollen, house dust, animal dandruff, moulds, etc. Allergic diseases in which type I reactions play a significant role include asthma, eczema (atopic dermatitis), urticaria, allergic rhinitis and anaphylaxis.

Type II hypersensitivity reactions are caused by cell surface or tissue bound antibodies (IgG and IgM) and play a significant role in the pathogenesis of myasthenia gravis, Goodpasture's syndrome and Addisonian pernicious anaemia.

Type III hypersensitivity reactions (immune complex) are caused by autoantigens or exogenous antigens, such as certain bacteria, fungi and parasites. Diseases in which type III hypersensitivity reactions play a significant role include lupus erythematosus, rheumatoid arthritis and glomerulonephritis.

Type IV hypersensitivity reactions (delayed) are caused by cell or tissue bound antigens. This type of hypersensitivity plays a significant role in a number of conditions, e.g. graft-versus-host disease, leprosy, contact dermatitis and reactions due to insect bites.

A number of drug classes are available for the treatment of hypersensitivity reactions. Some of these are systemic and some are applied topically.

The corticosteroids are among the most widely used drugs for the treatment of hypersensitivity diseases. Corticosteroids primarily exert their pharmacological action by non-selectively inhibiting the function and proliferation of different classes of immune cells. Hereby hypersensitivity reactions are suppressed. Unfortunately the corticosteroids are associated with a number of serious side effects e.g. immunosuppression, osteoporosis and skin atrophy (when applied topically).

SUMMARY OF THE INVENTION

Surprisingly we have discovered synergistic pharmacological effects between certain groups of compounds that may be obtained from *Alpinia galanga*.

Thus we have found synergistic effects between aromatic compounds selected from the group consisting of 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol, and terpenoids selected from the group consisting of 1,8-cineol, α-pinene, β-pinene, limonene, α-terpineol, terpene-4-ol, and trans-β-farnesene. The latter group of terpenoids are the principal components of the volatile oil of *Alpinia galanga*.

Such synergistic effects are clearly demonstrated in Example 1.

Furthermore, we have found synergistic effects between the quantitatively dominating aromatic compound 1'-acetoxychavicol acetate and other aromatic compounds selected from the group consisting of 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol. Such synergistic effects are clearly demonstrated in Example 2.

We have found that the above mentioned compositions significantly suppress hypersensitivity reactions. Compared to the corticosteroids the above mentioned compositions have the advantage of not being associated with any serious side effects.

The above mentioned synergistic effects between components of *Alpinia galanga* have never been described before. Furthermore synergistic compositions containing such compounds have never been described before.

Accordingly the present invention provides a composition of matter containing:

a) 2–99.5% (w/w) of one or more compounds selected from the group consisting of 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol;

b) 0.5–98% (w/w) of one or more compounds selected from the group consisting of 1,8-cineol, α-pinene, α-pinene, limonene, α-terpineol, terpene-4-ol, and trans-β-farnesene.

Furthermore the invention provides a composition of matter, preferably in the form of an extract or concentrate of *Alpinia galanga*, containing:

a) 2–99.5% (w/w) of one or more compounds selected from the group consisting of 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol;

b) 0.5–98% (w/w) essential oil of *Alpinia galanga* or mixtures thereof.

Also the invention provides a composition of matter containing:

a) 2–99.5% (w/w) 1'-acetoxychavicol acetate;

b) 0.5–98% (w/w) of one or more compounds selected from the group consisting of 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol.

Due to their pharmacological effects the above mentioned synergistic compositions can be employed for the following therapeutic applications:

Immunomodulation.

Treatment or prevention of hypersensitivity diseases.

Treatment or prevention of IgE mediated allergic reactions and conditions.

Treatment or prevention of autoimmune disorders.

Alleviation of pain.

Accordingly the present invention provides a pharmaceutical, a cosmetic or a dietary supplement containing the above mentioned compositions and a pharmaceutically or cosmetically acceptable carrier.

More specifically the present invention provides the use of the above mentioned compositions for preparing a medicament for immunomodulation, for the suppression of hypersensitivity reactions such as IgE mediated allergic reactions and autoimmune reactions, and for the alleviation of pain.

Thus, according to the invention the above mentioned compositions can be used in a method for the treatment or prevention of a hypersensitivity disease in an individual, which comprises administering such composition or a pharmaceutical containing it to said individual; and the invention comprises the use of the above mentioned compositions for preparing a medicament for the treatment or prevention of hypersensitivity diseases.

Also, according to the invention the above mentioned compositions can be used in a method for the treatment or prevention of an autoimmune disorder in an individual, which comprises administering such composition or a pharmaceutical containing it to said individual; and the invention comprises the use of the above mentioned compositions for preparing a medicament for the treatment or prevention of autoimmune disorders.

Further, according to the invention the above mentioned compositions can be used in a method for the treatment or prevention of an IgE mediated allergic reaction or condition in an individual, which comprises administering such composition or a pharmaceutical containing it to said individual; and the invention comprises the use of the above mentioned compositions for preparing a medicament for the treatment or prevention of IgE mediated allergic reactions and conditions.

Also, according to the invention the above mentioned compositions can be used in a method for the alleviation of pain in an individual, which comprises administering such composition or a pharmaceutical containing it to said individual; and the invention comprises the use of the above mentioned compositions for preparing a medicament for the alleviation of pain.

Further, the invention provides a method of preparing the above mentioned compositions, which comprises distilling and/or extracting *Alpinia galanga* or parts thereof, preferably the rhizome, with an extraction agent comprising an organic solvent and subsequently, if necessary, removing the extraction agent to obtain an extract suitable for utilisation.

DETAILED DESCRIPTION OF THE INVENTION

Surprisingly we have discovered synergistic pharmacological effects between aromatic compounds selected from the group consisting of 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol, and terpenoids selected from the group consisting of 1,8-cineol, α-pinene, β-pinene, limonene, α-terpineol, terpene-4-ol, and trans-β-farnesene. The latter group of terpenoids are the principal components of the volatile oil of *Alpinia galanga*.

Such synergistic effects are clearly demonstrated in Example 1, where the composition according to the invention shows pharmacological effects far superior to its components.

Furthermore we have found synergistic effects between the quantitatively dominating aromatic compound of *Alpinia galanga* 1'-acetoxychavicol acetate, and other aromatic compounds selected from the group consisting of 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol.

Such synergistic effects are clearly demonstrated in Example 2, where the composition according to the invention shows pharmacological effects far superior to its components.

Surprisingly we have found that such synergistic compositions exert pharmacological actions relevant to the therapeutic treatment of conditions associated with hypersensitivity reactions and pain.

More specifically the above mentioned compositions provide the following pharmacological effects upon administration to the living organism:

Immunomodulation.

Suppression of hypersensitivity reactions.

Suppression of IgE mediated allergic reactions.

Suppression of autoimmune reactions.

Reduction of pain.

Accordingly the present invention provides a composition of matter containing:
- a) 2–99.5% (w/w) of one or more compounds selected from the group consisting of 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol;
- b) 0.5–98% (w/w) of one or more compounds selected from the group consisting of 1,8-cineol, α-pinene, β-pinene, limonene, α-terpineol, terpene-4-ol, and trans-β-farnesene.

The percentage (w/w) of compounds selected from the group consisting of 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol in the composition is typically at least 2.0%, e.g. at least 2.5%, at least 3.0%, at least 4.0%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, or at least 40.0%, and most preferably at least 50.0% e.g. at least 75.0%.

The percentage (w/w) of compounds selected from the group consisting of 1,8-cineol, α-pinene, β-pinene, limonene, α-terpineol, terpene-4-ol, and trans-β-farnesene in the composition is typically at least 0.5%, e.g. at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, or at least 40.0%, and most preferably at least 50.0%, e.g. at least 75.0%.

Furthermore the present invention provides a composition of matter, preferably in the form of an extract or concentrate of Alpinia galanga, containing:
- a) 2–99.5% (w/w) of one or more compounds selected from the group consisting of 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol;
- b) 0.5–98% (w/w) essential oil of Alpinia galanga or mixtures thereof.

The percentage (w/w) of compounds selected from the group consisting of 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol in the composition is typically at least 2.0%, e.g. at least 2.5%, at least 3.0%, at least 4.0%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, or at least 40.0%, and most preferably at least 50.0% e.g. at least 75.0%.

The percentage (w/w) of essential oil of Alpinia galanga in the composition is typically at least 0.5%, e.g. at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, or at least 40.0%, and most preferably at least 50.0%, e.g. at least 75.0%.

Also the present invention provides a composition of matter containing:
- a) 2–99.5% (w/w) 1'-acetoxychavicol acetate;
- b) 0.5–98% (w/w) of one or more compounds selected from the group consisting of 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol.

The percentage (w/w) of 1'-acetoxychavicol acetate in the composition is typically at least 2.0%, e.g. at least 2.5%, at least 3.0%, at least 4.0%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, or at least 40.0%, and most preferably at least 50.0% e.g. at least 75.0%.

The percentage (w/w) of one or more compounds selected from the group consisting of 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol and 3,4-dimethoxy-trans-cinnamylalcohol in the composition is typically at least 0.5%, e.g. at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, or at least 40.0%, and most preferably at least 50.0%, e.g. at least 75.0%.

The synergistic compositions according to the invention are new and superior to their components, when these are used alone, e.g. 1'-acetoxychavicol acetate (see Example 2).

The components of the compositions according to the invention may be obtained from other plants than Alpinia galanga. For example, some of the terpenoids to be used in the compositions may be derived from plants of the Labiatae family, e.g. α-terpineol from Thymus vulgaris or Origanum cordifolium, and trans-β-farnesene from Mentha piperita. Also, the terpenoids may be obtained from plants of other families. Specifically, 1,8-cineol may be derived from Eucalyptus globulus, Achillea distans or Melaleuca alternifolia; α-pinene/β-pinene may be derived from Achillea distans; and α-terpineol may be derived from Melaleuca alternifolia. Further, the aromatic compounds to be used in the compositions may for example be derived from other plants of the Zingiberaceae family, e.g. Alpinia conchigera. Again, plants of other families may be employed as sources of the aromatic compounds, e.g. 1'-hydroxychavicol may be derived from Piper betel. Furthermore, a number of the substances to be used as components of the compositions according to the invention can be produced synthetically.

Furthermore, the invention provides novel pharmaceuticals, cosmetics or dietary supplements with specific chemical compositions.

A "dietary supplement" is defined according to the U.S. Food and Drug Administration in the Dietary Supplement Health and Education Act of 1994 (DSHEA). The DSHEA gives the following formal definition of a "dietary supplement":

"A dietary supplement is a product (other than tobacco) that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract, or combinations of these things that is intended for ingestion in pill, capsule, tablet, or liquid form."

Similar definitions exist in other parts of the world, e.g. in Europe; in the present context, the definition is as defined above. Different denominations concerning "dietary supplements" are used around the world, such as "food supplements", "neutraceuticals", "functional foods" or simply "foods". In the present context the term "dietary supplement" covers any such denomination or definition.

Accordingly the present invention provides a pharmaceutical, a cosmetic or a dietary supplement comprising:
  a) 0.01–99.9% (w/w) of any of the above mentioned compositions according to the invention;
  b) 0.1–99.99% (w/w) of a pharmaceutically or cosmetically acceptable vehicle.

The percentage (w/w) of any of the above mentioned compositions in the pharmaceutical, cosmetic or dietary supplement is typically at least 0.01%, e.g. at least 0.025%, at least 0.05%, at least 0.1%, at least 0.25%, at least 0.5%, at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40.0%, and most preferably at least 50.0%, e.g. at least 75.0%.

Furthermore the present invention provides a pharmaceutical, a cosmetic or a dietary supplement comprising:
  a) 0.01–99.89% (w/w) any one of the above mentioned compositions according to the invention;
  b) 0.01–99.89% (w/w) of *Zingiber officinale* or parts, extracts or components thereof;
  c) 0.1–99.98% (w/w) of a pharmaceutically or cosmetically acceptable vehicle.

The percentage (w/w) of any of the above mentioned compositions in the pharmaceutical, cosmetic or dietary supplement is typically at least 0.01%, e.g. at least 0.025%, at least 0.05%, at least 0.1%, at least 0.25%, at least 0.5%, at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40.0%, and most preferably at least 50.0%, e.g. at least 75.0%.

The percentage (w/w) of *Zingiber officinale* or parts, extracts or components thereof in the composition is typically at least 0.01%, e.g. at least 0.025%, at least 0.05%, at least 0.1%, at least 0.25%, at least 0.5%, at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40.0%, and most preferably at least 50.0%, e.g. at least 75.0%.

Also the present invention provides a pharmaceutical, a cosmetic or a dietary supplement comprising:
  a) 0.01–99.89% (w/w) of any of the above mentioned compositions according to the invention;
  b) 0.01–99.89% (w/w) of γ-linolenic acid or eicosapentaenoic acid, eventually in the form of vegetable oil or fish oil;
  c) 0.1–99.98% (w/w) of a pharmaceutically acceptable vehicle.

The percentage (w/w) of any of the above mentioned compositions in the pharmaceutical, cosmetic or dietary supplement is typically at least 0.01%, e.g. at least 0.025%, at least 0.05%, at least 0.1%, at least 0.25%, at least 0.5%, at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40.0%, and most preferably at least 50.0%, e.g. at least 75.0%.

The percentage (w/w) of γ-linolenic acid or eicosapentaenoic acid, optionally in the form of vegetable oil or fish oil, in the composition is typically at least 0.01%, e.g. at least 0.025%, at least 0.05%, at least 0.1%, at least 0.25%, at least 0.5%, at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40.0%, and most preferably at least 50.0%, e.g. at least 75.0%.

Further, the present invention provides a pharmaceutical, a cosmetic or a dietary supplement comprising:
  a) 0.01–99.89% (w/w) of the aforementioned compositions, i.e., those described at page 9, lines 17 to 27; page 10, lines 20 to 28; and page 11, lines 19 to 25;
  b) 0.01–99.89% (w/w) of at least one isoflavone selected from the group consisting of biochanin A, formononetin, pratensein, trifoside, pectolinarin, daidzin, 6"-OAc daidzin, 6"-OMal daidzin, daidzein, genistin, 6"-OAc genistin, 6"-OMal genistin, genisein, glycitin, 6"-OAc glycitin, 6"-OMal glycitin, glycitein, puerarin and calycosine galactoside, and derivatives or metabolites thereof, and
  c) 0.1–99.98% (w/w) of a pharmaceutically or cosmetically acceptable vehicle.

Such pharmaceutical compositions or dietary supplements are particularly relevant for the management of Premenstrual syndrome (PMS), premenstrual tension or menopausal disorders.

The percentage (w/w) of any of the above mentioned compositions in the pharmaceutical, cosmetic or dietary supplement is typically at least 0.01%, e.g. at least 0.025%, at least 0.05%, at least 0.1%, at least 0.25%, at least 0.5%, at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40.0%, and most preferably at least 50.0%, e.g. at least 75.0%.

The percentage (w/w) of isoflavone component in the composition is typically at least 0.01%, e.g. at least 0.025%, at least 0.05%, at least 0.1%, at least 0.25%, at least 0.5%, at least 1.0%, at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40.0%, and most preferably at least 50.0%, e.g. at least 75.0%.

Still further, the present invention provides a pharmaceutical, a cosmetic or a dietary supplement comprising:
  a) 0.01–99.89% (w/w) of a composition according to any one of claims 1–3;

b) 0.01–99.89% (w/w) of at least one cartilage component selected from the group consisting of chondroitin sulfate, glucosamine, glucos amine sulfate or derivatives thereof;

c) 0.1–99.98% (w/w) of a pharmaceutically or cosmetically acceptable vehicle.

Such pharmaceutical compositions or dietary supplements are particularly relevant for the management of arthritis, e.g. osteoarthritis or rheumatoid arthritis.

The percentage (w/w) of any of the above mentioned compositions in the pharmaceutical, cosmetic or dietary supplement is typically at least 0.01%, e.g. at least 0.025%, at least 0.05%, at least 0.1%, at least 0.25%, at least 0.5%, at least 1.0%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40%, and most preferably at least 50.0%, e.g. at least 75.0%.

The percentage (w/w) of cartilage component in the composition is typically at least 0.01%, e.g. at least 0.025%, at least 0.05%, at least 0.1%, at least 0.25%, at least 0.5%, at least 2.5%, at least 5.0%, or at least 7.5%, preferably at least 10.0%, e.g. at least 12.5%, at least 15.0%, or at least 17.5%, more preferably at least 20.0%, e.g. at least 25.0%, at least 30.0%, at least 35.0%, or at least 40.0%, and most preferably at least 50.0%, e.g. at least 75.0%.

The above mentioned effects provide part of the rationale for the following therapeutic applications of the above mentioned compositions according to the invention:

A method for the treatment or prevention of hypersensitivity diseases characterised by the administration of the above mentioned compositions. The therapeutic action may be relevant to all known diseases associated with hypersensitivity reactions. In the following autoimmune disorders and IgE mediated allergic conditions are described in more detail. In addition to these specific therapeutic areas the action of the above mentioned compositions is relevant to all known conditions and diseases associated with hypersensitivity reactions, such as infections (viral, bacterial, fungal, parasitic, etc.), cold and flu, contact dermatitis, insect bites, allergic vasculitis, postoperative reactions, transplantation rejection (graft-versus-host disease), etc., and the following examples are not limiting with respect to this.

A method for the treatment or prevention of autoimmune disorders characterised by the administration of the above mentioned compositions. The applicant puts forward the hypothesis that the therapeutic action is due to the immunomodulating and suppressing effect of the above mentioned compositions on hypersensitivity reactions. The therapeutic action may be relevant to all known autoimmune disorders such as autoimmune hepatitis, primary biliary cirrhosis, primary sclerosing cholangitis, autoimmune hemolytic anemias, Grave's disease, myasthenia gravis, type 1 diabetes mellitus, inflammatory myopathies, multiple sclerosis, Hashimoto's thyreoiditis, autoimmune adrenalitis, Crohn's disease, ulcerative colitis, glomerulonephritis, progressive systemic sclerosis (scleroderma), Sjögren's disease, lupus erythematosus, primary vasculitis, rheumatoid arthritis, juvenile arthritis, mixed connective tissue disease, psoriasis, pemfigus, pemfigoid, dermatitis herpetiformis, etc., and the following examples are not limiting with respect to this.

A method for the treatment or prevention of IgE mediated allergic reactions and conditions characterised by the administration of the above mentioned compositions. The applicant puts forward the hypothesis that the therapeutic action is due to the suppressing effect of the above mentioned compositions on hypersensitivity reactions. The therapeutic action may be relevant to all known IgE mediated allergic reactions and conditions such as asthma, eczema (e.g. atopic dermatitis), urticaria, allergic rhinitis, anaphylaxis, etc., and the following examples are not limiting with respect to this.

A method for the treatment or prevention of any condition associated with pain characterised by the administration of the above mentioned compositions. The applicant puts forward the hypothesis that the therapeutic action is related to immunomodulation, possibly to suppressing effects on hypersensitivity reactions.

The preferred embodiment of the invention is an extract or concentrate of *Alpinia galanga*. Extracts according to the invention can i.a. be obtained by extraction or distillation (e.g. hydro, steam or vacuum distillation) of fresh or dried *Alpinia galanga* or parts thereof, preferably the rhizome. Extraction may be performed with a number of different organic solvents, preferably water miscible solvents, and mixtures thereof with water. The extraction can be performed hot or cold by the employment of any extraction technology e.g. maceration, percolation or supercritical extraction (e.g. with carbon dioxide).

The preferred extraction solvents are acetone, methyl ethyl ketone, methyl acetate, ethyl acetate, lower alkanols having 1–4 carbon atoms, pentane, hexane, heptane and mixtures thereof. The preferred extraction temperature is close to the boiling point of the employed solvent due to extraction efficacy, but lower temperatures are also applicable making necessary a longer period of extraction.

By changing the composition of the applied solvent the extraction can be made more selective for certain constituents of *Alpinia galanga* thus enhancing or reducing their content in the finished extract.

After the primary extraction process a second step of processing, such as liquid—liquid extraction, column chromatography or any type of distillation, can be employed to remove or to concentrate and possibly isolate any constituent of the extract. Hereby any constituent of *Alpinia galanga* can be avoided or concentrated in the finished extract, e.g. 1,8-cineol, α-pinene, β-pinene, limonene, α-terpineol, terpene-4-ol, trans-β-farnesene, 1'-acetoxychavicol acetate, 1'-acetoxyeugenol acetate, trans-p-coumaryl diacetate, coniferyl diacetate, 1'-hydroxychavicol acetate, 1'-hydroxychavicol, p-hydroxy-trans-cinnamaldehyde, p-methoxy-trans-cinnamylalcohol, 3,4-dimethoxy-trans-cinnamylalcohol, galangal A, galangal B, galanolactone, labda-8(17)-12-diene-15,16-dial and 8-17-epoxylabd-12-ene-15,16-dial. Thus the content of any component can be standardised to obtain a synergistic composition according to the invention.

According to the invention the above mentioned compositions can be combined with any other active ingredient or plant extract to potentiate the therapeutic action. Consequently, we propose to combine the synergistic compositions of the invention with eicosapentaenoic acid (e.g. obtained from from fish oils) or γ-linolenic acid (e.g. obtained from *Borago officinalis*) for any of the above mentioned therapeutic applications. As a parallel, we propose to combine the compositions of the invention with *Zingiber officinale* or parts thereof or extracts or components thereof for the same therapeutic applications.

Furthermore it is obvious that in the use according to the invention for preparing medicaments the above mentioned compositions may be mixed with additives such as surfactants, solvents, thickeners, stabilisers, preservatives, antioxidants, flavour etc. to obtain a desirable product formulation. Similarly, the pharmaceutical compositions according to the invention may further contain such additives. There are no limitations to the route of administration or dosage form of the formulation and the following examples are not limiting with respect to this: tablets, capsules, fluids, granulates, gels, ointments, emulsions (e.g. cremes and lotions), sprays (e.g. aerosol), eye drops, etc. Optionally, the composition may also contain surfactants such as bile salts, polyoxyethylene-sorbitan-fatty acid esters or polyalcohol mixed chain-length fatty acid esters for improving dispersibility of the composition in the digestive fluids leading to improved bioavailability or for obtaining the final dosage form of the composition.

EXAMPLES

Example 1

Study Object

A composition according to the invention was tested in this study for inhibitory activity in three enzyme inhibition assays, Leukotriene C4 Synthetase, 5-Lipoxygenase and Phosphodiesterase-IV, respectively. The composition comprising a 1:1 mixture of a concentrate of terpenoids and a concentrate of aromatic compounds derived from *Alpinia galanga* was compared to its two components to identify possible synergistic effects.

Study Summary

Background

The objective of the study was to establish the activity of a composition according to the invention in the lipoxygenase pathway and as a phosphodiesterase-IV (PDE IV) inhibitor.

Leukotriene C4 (LTC4) synthetase and 5-Lipoxygenase are enzymes involved in the lipoxygenase pathway. Leukotriene C4 (LTC4) synthetase is involved in the formation of LTC4 from LTA4. 5-Lipoxygenase catalyzes the oxidative metabolism of arachidonic acid to 5-hydroxyeicosatetraenoic acid (5-HETE), the initial reaction leading to formation of leukotrienes. Thus, taken together these assays may establish the degree of activity as well as a locus of action for agents which inhibit the formation of leukotrienes.

Phosphodiesterase type IV (PDE IV) catalyses the conversion of cAMP or cGMP to their respective monophosphate forms. PDE IV is insensitive to Ca2+/calmodulin or cGMP regulation, exihibits a cAMP substrate dependence, and is inhibited by the specific inhibitor RO 20-1724. Since cyclic nucleotides are important second messengers in the cells of many tissues and organs, development of therapeutics that selectively target specific PDE isoforms is considered an important goal. PDE IV is believed to be the most important PDA isoform in bronchial relaxation, allergy and inflammation. Inhibitors for PDE IV are therefore considered valuable agents in the treatment of astma, allergy and inflammatory disease.

Methods

Test Compounds

A terpenoid concentrate (referred to as Compound A in the following) of *Alpinia galanga* was prepared by steam distillation of dry powdered rhizome. The presence of key terpenoids was confirmed by GC-MS.

A concentrate of aromatic compounds (referred to as Compound B in the following) from *Alpinia galanga* was prepared by percolation of dry powdered rhizome with acetone and hexane, and subsequently removing the extraction solvent by evaporation under vacuum. Residues of volatile oil were removed by flash chromatography.

A composition according to the invention (referred to as Compound C in the following) was prepared by mixing compound A and B (1:1 by weight).

Leukotriene C4 Synthetase Assay

LTC4 synthase prepared as a crude fraction from guinea pig lung was used. The test compounds were tested in duplicate at a concentration of 300 $\mu$g/ml. The test compound and/or vehicle was incubated with 12 $\mu$g enzyme, 0.3 $\mu$g LTA4 methyl ester, 0.2% (w/w) albumin (to stabilize the product) and 4.5 mM serine borate (to prevent conversion of LTC4 to LTD4) in phosphate buffer pH 7.8 for 30 minutes at 37° C. The reaction was terminated by addition of ice-cold methanol. Formation of LTC4 was quantitated by RIA (radioimmunoassay).

5-Lipoxygenase Assay

A crude 5-lipoxygenase enzyme preparation from rat basophilic leukemia cells (RBL-1) was used. The test compounds were tested in duplicate at a concentration of 9 $\mu$g/ml. The test compound and/or vehicle was pre-incubated with enzyme for 5 minutes in Tris buffer pH 7.2 at room temperature. The reaction was initiated by addition of 15 $\mu$M arachidonic acid as substrate and continued for an additional 8 minutes after which the reaction was terminated by addition of 70 mM citric acid. The formation of 5-HETE was quantitated by RIA.

Phosphodiesterase-IV Assay

PDE-IV partially purified from human U937 pronocytic cells was used. The test compounds were tested in duplicate at a concentration of 30 $\mu$g/ml. Test compound and/or vehicle was incubated with 40 $\mu$g enzyme and 1 $\mu$g cAMP containing 0.01 $\mu$M [$^3$H]cAMP in Tris buffer pH 7.5 for 20 minutes at 30° C. The reaction was terminated by boiling for 2 minutes and the resulting AMP was converted to adenosine by addition of 10 mg/ml snake venom nucleotidase and further incubation at 30° C. for 10 minutes. Unhydrolysed cAMP is bound to AGI-X2 resin, and remaining [$^3$H] adenosine in the aqueous phase is quantitated by scintillation counting.

Findings

Results are presented in table 1 (percentage inhibition compared to a control without test compound).

TABLE 1

| Test Compound | Assay | Inhibition % |
| --- | --- | --- |
| Compound A | LTC4 Synthetase | 25 |
| Compound B | LTC4 Synthetase | 21 |
| Compound C | LTC4 Synthetase | 32 |
| Compound A | 5-Lipoxygenase | −89 |
| Compound B | 5-Lipoxygenase | 16 |
| Compound C | 5-Lipoxygenase | 35 |
| Compound A | PDE-IV | 14 |
| Compound B | PDE-IV | 4 |
| Compound C | PDE-IV | 56 |

Interpretation

In this study the synergistic effect of the composition (compound C) is evaluated by comparing its effect to the mean effect of compounds A and B (the calculated additive effect of the two).

In the leukotriene C4 synthetase assay the effect of Compound C is 32% inhibition, which is 39% higher than the calculated additive effect of Compound A and B (23% inhibition). This clearly demonstrates a synergistic effect according to the invention.

In the 5-lipoxygenase assay the effect of Compound C is 35% inhibition, which is surprising as the calculated additive effect of Compound A and B is −37% inhibition. This clearly demonstrates a synergistic effect according to the invention.

In the phosphodiesterase-IV assay the effect of Compound C is 56% inhibition, which is 522% higher than the calculated additive effect of Compound A and B (9% inhibition). This clearly demonstrates a synergistic effect according to the invention.

Example 2

Study Object

A composition according to the invention was tested in this study for inhibitory activity in two enzyme inhibition assays, Leukotriene C4 Synthetase and Phosphodiesterase-IV, respectively. The composition comprising 1'-acetoxychavicol acetate and a concentrate of aromatic compounds derived from *Alpinia galanga* was compared to its two components to identify possible synergistic effects.

Study Summary

Background

The objective of the study was to establish the activity of a composition according to the invention in the lipoxygenase pathway and as a phosphodiesterase-IV (PDE IV) inhibitor.

Leukotriene C4 (LTC4) synthetase and 5-Lipoxygenase are enzymes involved in the lipoxygenase pathway. Leukotriene C4 (LTC4) synthetase is involved in the formation of LTC4 from LTA4. 5-Lipoxygenase catalyzes the oxidative metabolism of arachidonic acid to 5-hydroxyeicosatetraenoic acid (5-HETE), the initial reaction leading to formation of leukotrienes. Thus, taken together these assays may establish the degree of activity as well as a locus of action for agents which inhibit the formation of leukotrienes.

Phosphodiesterase type IV (PDE IV) catalyses the conversion of cAMP or cGMP to their respective monophosphate forms. PDE IV is insensitive to $Ca^{2+}$/calmodulin or cGMP regulation, exihibits a cAMP substrate dependence, and is inhibited by the specific inhibitor RO 20-1724. Since cyclic nucleotides are important second messengers in the cells of many tissues and organs, development of therapeutics that selectively target specific PDE isoforms is considered an important goal. PDE IV is believed to be the most important PDA isoform in bronchial relaxation, allergy and inflammation. Inhibitors for PDE IV are therefore considered valuable agents in the treatment of asthma, allergy and inflammatory disease.

Methods

Test Compounds

1'-acetoxychavicol acetate (referred to as Compound A in the following) was prepared by preparative HPLC. The purity of the compound was confirmed by GC-MS.

A concentrate of aromatic compounds (referred to as Compound B in the following) from *Alpinia galanga* was prepared by percolation of dry powdered rhizome with acetone and hexane, and subsequently removing the extraction solvent by evaporation under vacuum. Residues of volatile oil were removed by flash chromatography.

A composition according to the invention (referred to as Compound C in the following) was prepared by mixing compounds A and B (1:1 by weight).

Leukotriene C4 Synthetase Assay

LTC4 synthase prepared as a crude fraction from guinea pig lung was used. The test compounds were tested in duplicate at a concentration of 300 μg/ml. The test compound and/or vehicle was incubated with 12 μg enzyme, 0.3 μg LTA4 methyl ester, 0.2% (w/w) albumin (to stabilize the product) and 4.5 mM serine borate (to prevent conversion of LTC4 to LTD4) in phosphate buffer pH 7.8 for 30 minutes at 37° C. The reaction was terminated by addition of ice-cold methanol. Formation of LTC4 was quantitated by RIA (radioimmunoassay).

Phosphodiesterase-IV Assay

PDE-IV partially purified from human U937 pronocytic cells was used. The test compounds were tested in duplicate at a concentration of 30 μg/ml. Test compound and/or vehicle was incubated with 40 μg enzyme and 1 μg cAMP containing 0.01 μM [$^3$H]cAMP in Tris buffer pH 7.5 for 20 minutes at 30° C. The reaction was terminated by boiling for 2 minutes and the resulting AMP was converted to adenosine by addition of 10 mg/ml snake venom nucleotidase and further incubation at 30° C. for 10 minutes. Unhydrolysed cAMP is bound to AGI-X2 resin, and remaining [$^3$H] adenosine in the aqueous phase is quantitated by scintillation counting.

Findings

Results are presented in table 2 (percentage inhibition compared to a control without test compound).

TABLE 2

| Test Compound | Assay | Inhibition % |
| --- | --- | --- |
| Compound A | LTC4 Synthetase | 20 |
| Compound B | LTC4 Synthetase | 24 |
| Compound C | LTC4 Synthetase | 44 |
| Compound A | PDE-IV | 49 |
| Compound B | PDE-IV | 12 |
| Compound C | PDE-IV | 67 |

Interpretation

In this study the synergistic effect of the composition (Compound C) is evaluated by comparing the effect of Compound C to the mean effect of compounds A and B (the calculated additive effect of the two).

In the leukotriene C4 synthetase assay the effect of Compound C is 44% inhibition, which is 100% higher than the calculated additive effect of Compound A and B (22% inhibition). This clearly demonstrates a synergistic effect according to the invention.

In the phosphodiesterase-IV assay the effect of Compound C is 67% inhibition, which is 116% higher than the calculated additive effect of Compound A and B (31% inhibition). This clearly demonstrates a synergistic effect according to the invention.

Example 3

A pharmaceutical composition according to the invention was prepared as follows.

A composition according to the invention derived from *Alpinia galanga* comprising 80% of a concentrate of aromatic compounds and 20% of a terpenoid concentrate was formulated in a preparation for use as nasal drops or nasal spray, according to the following prescription:

For preparation of 100 g nasal spray, 1 mg/ml:

| | |
| --- | --- |
| a) Aromatic/terpenoid composition: | 0.05 g |
| b) Cremophor RH 40, BASF: | 2.00 g |
| c) Ethylenediamine tetraacetic acid, Fluka: | 0.05 g |
| d) Benzalkonium chloride, Sigma: | 0.01 g |
| e) Sodium chloride, Merck: | 0.89 g |
| f) Milli Q water, Millipore: | 97.00 g |

Procedure a) is dispersed in b) while heated to 37° C. on a water bath; c), d) and e) are added. After mixing, f) is added little by little under vigorous mixing.

A nasal spray formulation, prepared according to the above prescription, was tested by 4 volunteers. The nasal spray was reported to be effective against allergic rhinitis.

Example 4

A pharmaceutical composition according to the invention was prepared as follows.

A composition according to the invention derived from *Alpinia galanga* comprising 50% of a concentrate of aromatic compounds and 50% of a terpenoid concentrate was formulated in an ointment base according to the following prescription:

For preparation of 30 g ointment, 0,5% (w/w):

| | |
|---|---|
| a) Aromatic/terpenoid composition | 0.3 g |
| b) Cremeol E-45, Århus Oliefabrik A/S: | 19.5 g |
| c) Volatile Silicone VS72, Bionord A/S: | 9.0 g |
| d) Cremeol HF-52 SPC, Århus Oliefabrik A/S: | 1.2 g |

Procedure d) is melted at approx. 100° C.; and b) is added under continuous heating and mixing. Then c) is added, and the mixture is cooled to room temperature. Finally a) is added, and the formulation is mixed.

The ointment formulation, prepared according to the above prescription was tested by 5 volunteers suffering from atopic eczema. The ointment was reported to be effective against symptoms of atopic eczema.

Example 5

A pharmaceutical composition according to the invention was prepared as follows.

A composition according to the invention derived from *Alpinia galanga* comprising 85% of a concentrate of aromatic compounds and 15% of a terpenoid concentrate was mixed with an acetone extract of *Zingiber officinale* and formulated in a vegetable oil according to the following prescription:

For preparation of 100 g soft gelatine capsule fill:

| | |
|---|---|
| a) Aromatic/terpenoid composition: | 15.0 g |
| b) Zingiber officinale extract: | 20.0 g |
| c) Peanut oil, Aarhus Oliefabrik A/S: | 65.0 g |

Procedure a), b) and c) are mixed vigorously.

Gelatine capsules containing 350 mg of the fill, prepared according to the above prescription, were tested by 5 volunteers suffering from osteoarthritis. After two weeks of administration (two capsules a day) all volunteers reported a reduction of their pain.

What is claimed is:

1. A pharmaceutical, a cosmetic or a dietary supplement consistently essentially of 0.01–99.9% (w/w) of a synergistic composition containing:

a) 2–99.5% (w/w) 1'-acetoxychavicol acetate;
   b) 0.5–98% (w/w) of one or more compounds selected from the group consisting of trans-p-coumaryl diacetate, coniferyl diacetate, 1'-hydroxychavicol, p-hydroxy-trans-cinnamaldehyde, p-methoxy-trans-cinnamylalcohol and 3,4-dimethoxy-trans-cinnamylalcohol;
   and 0.1–99.99% (w/w) of a pharmaceutically acceptable vehicle.

2. A pharmaceutical, a cosmetic or a dietary supplement of claim 1, wherein the composition is an extract of *Alpinia galanga*, wherein the extract is prepared by extraction with organic solvents or with mixtures of water miscible organic solvents and water or by distillation of *Alpinia galanga*.

3. A method for the treatment or prevention of a hypersensitivity disease in an individual, which comprises administering a pharmaceutical of claim 1 to said individual.

4. A method for the treatment or prevention of an autoimmune disorder in an individual, which comprises administering a pharmaceutical of claim 1 to said individual.

5. A method for the treatment or prevention of an IgE mediated allergic reaction or condition in an individual, which comprises administering a pharmaceutical of claim 1 to said individual.

6. A method for the alleviation of pain in an individual, which comprises administering a pharmaceutical of claim 1 to said individual.

7. A method of preparing a composition of claim 1, which comprises distilling fresh or dried *Alpinia galanga* or parts thereof and/or extracting said plant material with an extraction agent comprising one or more organic solvents or mixtures thereof with water and subsequently, if necessary, removing the extraction agent.

8. A method of claim 7, wherein the *Alpinia galanga* or the parts thereof is the rhizome.

9. A method according to claim 7, wherein said organic solvent is selected from the group consisting of acetone, methyl ethyl ketone, methyl acetate, ethyl acetate, lower alkanols having 1–4 carbon atoms, pentane, hexane, heptane and mixtures thereof.

10. A method according to claim 7 wherein the composition is further subjected to liquid—liquid extraction or chromatography for the removal or concentration of certain constituents.

* * * * *